(12) United States Patent
Isezaki et al.

(10) Patent No.: US 11,687,554 B2
(45) Date of Patent: Jun. 27, 2023

(54) MULTIDIMENSIONAL DATA VISUALIZATION APPARATUS, METHOD, AND PROGRAM

(71) Applicant: NIPPON TELEGRAPH AND TELEPHONE CORPORATION, Tokyo (JP)

(72) Inventors: Takashi Isezaki, Musashino (JP); Ryosuke Aoki, Musashino (JP); Tomoki Watanabe, Musashino (JP); Tomohiro Yamada, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 1 day.

(21) Appl. No.: 17/282,182

(22) PCT Filed: Sep. 20, 2019

(86) PCT No.: PCT/JP2019/036886
§ 371 (c)(1),
(2) Date: Apr. 1, 2021

(87) PCT Pub. No.: WO2020/071143
PCT Pub. Date: Apr. 9, 2020

(65) Prior Publication Data
US 2022/0012262 A1    Jan. 13, 2022

(30) Foreign Application Priority Data
Oct. 4, 2018    (JP) .............................. JP2018-189363

(51) Int. Cl.
*G06F 16/26*    (2019.01)
*G06F 16/28*    (2019.01)
(Continued)

(52) U.S. Cl.
CPC ................ *G06F 16/26* (2019.01); *A61B 5/11* (2013.01); *A61B 5/7264* (2013.01);
(Continued)

(58) Field of Classification Search
None
See application file for complete search history.

(56) References Cited

U.S. PATENT DOCUMENTS

2020/0075167 A1*    3/2020    Srivastava ............. G16H 20/30
2022/0011855 A1*    1/2022    Hazra .................. G06F 3/04845

OTHER PUBLICATIONS

Chu et al., "A Real-Time EMG Pattern Recognition System Based on Linear-Nonlinear Feature Projection fora Multifunction Myoelectric Hand", 2006 (Year: 2006).*
(Continued)

*Primary Examiner* — Dawaune A Conyers
(74) *Attorney, Agent, or Firm* — Harness, Dickey & Pierce, P.L.C.

(57) ABSTRACT

An embodiment of the present invention is provided with a projective transform model including a plurality of nodes and a projection table, the plurality of nodes each holding a reference vector having a dimension corresponding to the dimension of multi-dimensional data. The projection table indicates the correspondence relation between the number of each node and a coordinate in a two-dimensional space as a projection target of the reference vector held by the node. First in a learning phase, multi-dimensional input data of a positive example and a negative example is acquired, the amplitude characteristic amounts thereof are calculated, and this amplitude characteristic amount data is learned as the reference vectors of the nodes for each sample. Subsequently, the Euclidean distance between coordinates when the nodes learned based on the amplitude characteristic amount data of the positive example and the nodes learned based on the amplitude characteristic amount data of the
(Continued)

negative example are projected into the two-dimensional space in accordance with the projection table is calculated, and coordinates in the projection table are updated so that the calculated Euclidean distance becomes equal to or larger than a threshold value.

9 Claims, 10 Drawing Sheets

(51) Int. Cl.
  *G06F 16/22* (2019.01)
  *A61B 5/11* (2006.01)
  *A61B 5/00* (2006.01)
(52) U.S. Cl.
  CPC ...... *G06F 16/2264* (2019.01); *G06F 16/2282* (2019.01); *G06F 16/287* (2019.01)

(56) References Cited

OTHER PUBLICATIONS

Xiong et al., "An User-Independent Gesture Recognition Method Based on sEMG Decomposition", 2015; (Year: 2015).*
Hiroki Yokota et al., Visualization of human motion information using self-organizing map (Motor skill map involving optimized motion based on musculoskeletal model simulation), Proceedings of the Japan Society of Mechanical Engineers, vol. 82, No. 834, 2016.

* cited by examiner

Fig. 9

| NODE NUMBER | 1 | 2 | ... | 18 | ... | 33 | ... | K | ... | 75 | 76 | ... | 100 |
|---|---|---|---|---|---|---|---|---|---|---|---|---|---|
| COORDINATE VALUE | (0,0) | (1,0) | ... | (7,1) | ... | (2,3) | ... | (p,q) | ... | (4,7) | (5,7) | ... | (9,9) |

Fig. 12

| NODE NUMBER | 1 | 2 | ... | 18 | ... | 33 | ... | K | ... | 75 | 76 | ... | 100 |
|---|---|---|---|---|---|---|---|---|---|---|---|---|---|
| COORDINATE VALUE | (0,0) | (1,0) | ... | (7,1) | ... | (2,3) | ... | (p,q) | ... | (4,7) | (6,7) | ... | (9,9) |

MULTIDIMENSIONAL DATA VISUALIZATION APPARATUS, METHOD, AND PROGRAM

CROSS-REFERENCE TO RELATED APPLICATIONS

This application is a 371 U.S. National Phase of International Application No. PCT/JP2019/036886 filed on Sep. 20, 2019, which claims priority to Japanese Application No. 2018-189363 filed on Oct. 4, 2018. The entire disclosures of the above applications are incorporated herein by reference.

TECHNICAL FIELD

An aspect of the present invention relates to a multi-dimensional data visualization device, a multi-dimensional data visualization method, and a multi-dimensional data visualization program that are used to visualize multi-dimensional temporally sequential data indicating, for example, muscle activity.

BACKGROUND ART

Recently, analysis of various kinds of body motions has been developed in, for example, the medical, welfare, and sport fields. A motion typically includes temporally sequential activity of a plurality of muscles. Thus, to achieve an ideal motion, it is needed to analyze temporally sequential activity of a plurality of muscles and adjust contraction, relaxation, and tension of each individual muscle at each moment. Muscle activity can be analyzed by measuring an electric signal, in other words, a myoelectric signal, passing through a muscle fiber along with contraction of a muscle. However, it is difficult to visually analyze multi-dimensional temporally sequential data such as a myoelectric signal.

Thus, for example, a disclosed technology visualizes a motion state by generating and presenting a map obtained by mapping multi-dimensional temporally sequential data into a two-dimensional space by using self-organizing mapping (SOM) (for example, refer to Non-Patent Literature 1).

CITATION LIST

Non-Patent Literature

Non-Patent Literature 1: Hiroki Yokota, Shigemichi Ohshima, Naoki Mizuno, "Visualization of human motion information using self-organizing map (Motor skill map involving optimized motion based on musculoskeletal model simulation)", Journal of Japan Society of Mechanical engineers, Vol. 82, No. 834, 2016, published on 2016 Feb. 25

SUMMARY OF THE INVENTION

Technical Problem

However, the technology disclosed in Non-Patent Literature 1 has a problem to be solved as described below. Specifically, motion states in reality include a state (quasi-positive example) close to an ideal motion state, and a state (negative example) detached from the ideal motion state. When a motion state is visualized, such motion states (quasi-positive example and negative example) in reality and the ideal motion state (positive example) are displayed in the two-dimensional space, but the technology disclosed in Non-Patent Literature 1 does not consider differentiation between a motion state in reality and the ideal motion state, and thus it has been sometimes difficult to determine the difference between the motion states.

The present invention is intended to solve the above-described problem and provide a technology of enabling clear determination of the difference among a plurality of visualized pieces of multi-dimensional data.

Means for Solving the Problem

A multi-dimensional data visualization device or method according to an aspect of the present invention uses a projective transform model including a plurality of nodes and a table, the plurality of nodes each holding a reference vector having a dimension identical to a dimension of input multi-dimensional data, the table storing information indicating a correspondence relation between each node and a coordinate in a projection target space. Then, the device or method acquires first and second multi-dimensional data for learning, extracts characteristic amounts from the acquired first and second multi-dimensional data, respectively, and updates the reference vector of each node based on the extracted characteristic amounts of the first and second multi-dimensional data. Then, the device or method calculates, based on the characteristic amounts of the first and second multi-dimensional data, a distance between each pair of coordinates when the updated nodes are projected into the projection target space in accordance with the table, and updates the table so that the distance is equal to or larger than a threshold value.

Effects of the Invention

According to an aspect of the present invention, it is possible to provide a technology of enabling clear determination of the difference among a plurality of visualized pieces of multi-dimensional data.

BRIEF DESCRIPTION OF DRAWINGS

FIG. 9 is a diagram illustrating an exemplary projection table.

FIG. 12 is a diagram illustrating an exemplary projection table after node coordinate values in the projection table illustrated in FIG. 9 are moved.

DESCRIPTION OF EMBODIMENTS

Embodiments of the present invention will be described below with reference to the accompanying drawings.

Embodiment (Exemplary Configuration)

Figure 1:
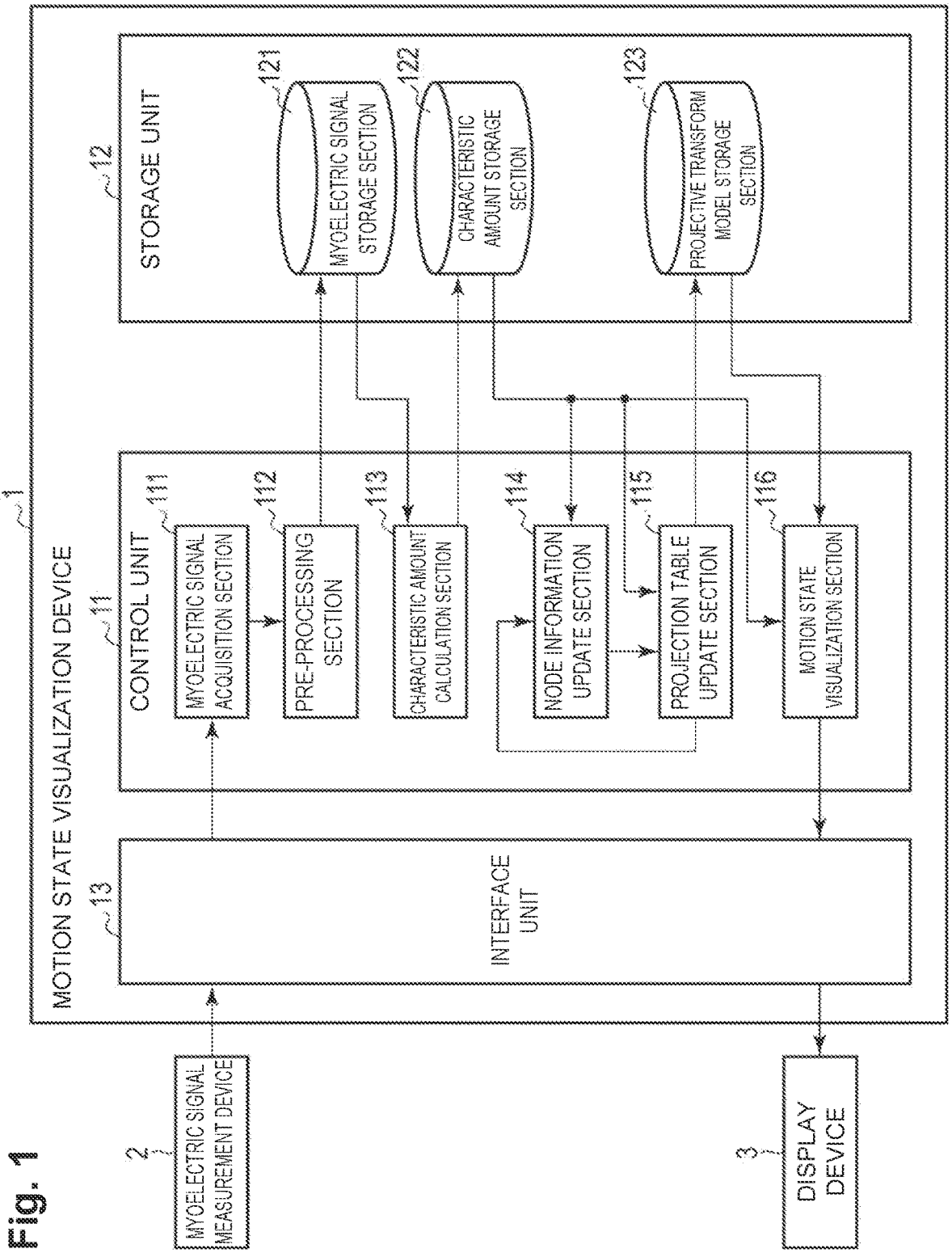
FIG. 1 is a block diagram illustrating a functional configuration of a motion state visualization device as an embodiment of a multi-dimensional data visualization device according to the present invention.

FIG. 1 is a block diagram illustrating a functional configuration of a motion state visualization device as an embodiment of a multi-dimensional data visualization device according to the present invention.

This motion state visualization device 1 is connected with a myoelectric signal measurement device 2 and a display device 3 through a signal cable, a local area network (LAN), or a wireless network such as a wireless LAN or Bluetooth (registered trademark).

For example, the myoelectric signal measurement device 2 has a function to output temporally sequential myoelectric signals continuously detected by electrodes mounted on a plurality of muscle sites corresponding to a monitoring-target muscle activity system of a subject.

The display device 3 is a terminal device including a display, such as a personal computer, a smartphone, a tablet terminal, or a wearable terminal and has a function to receive and display display data output from the motion state visualization device 1 and used to visualize a motion state.

The motion state visualization device 1 is, for example, a personal computer or a server computer and includes a control unit 11, a storage unit 12, and an interface unit 13. The interface unit 13 receives each myoelectric signal output from the myoelectric signal measurement device 2, transforms the myoelectric signal into, for example, waveform data made of a digital signal, and outputs the waveform data after the transform to the control unit 11. The interface unit 13 also outputs, to the display device 3, display data generated by the control unit 11 and used to visualize a motion state.

The storage unit 12 is configured as a combination of storage media including a non-transitory memory that is writable and readable as needed, such as a hard disk drive (HDD) or a solid-state drive (SSD), a non-transitory memory such as a read only memory (ROM), and a transitory memory such as a random-access memory (RAM). A computer program storage region and a data storage region are provided as storage regions of the storage unit 12. The computer program storage region stores computer programs necessary for executing various kinds of control processing according to the embodiment of the present invention.

A myoelectric signal storage section 121, a characteristic amount storage section 122, and a projective transform model storage section 123 are provided in the data storage region. The myoelectric signal storage section 121 is used to store the waveform data of each myoelectric signal acquired from the myoelectric signal measurement device 2, in other words, multi-dimensional temporally sequential data. The characteristic amount storage section 122 is used to store data indicating the characteristic amount of a waveform calculated from the waveform data of each myoelectric signal. The projective transform model storage section 123 is used to store a projective transform model generated by the control unit 10.

The control unit 10 includes, for example, a hardware processor such as a central processing unit (CPU) and includes, as control functions for achieving the embodiment of the present invention, a myoelectric signal acquisition section 111, a pre-processing section 112, a characteristic amount calculation section 113, a node information update section 114, a projection table update section 115, and a motion state visualization section 116. These control functions are each achieved by the hardware processor executing a computer program stored in the computer program storage region.

The myoelectric signal acquisition section 111 performs processing of acquiring, from the interface unit 13, the waveform data of each myoelectric signal output from the myoelectric signal measurement device 2, in other words, the multi-dimensional temporally sequential data. In this case, waveform data (positive-example data) corresponding to an ideal motion state and waveform data (negative-example data) corresponding to a motion state detached from the ideal motion state are prepared as the waveform data of each myoelectric signal and labeled as a positive example and a negative example, respectively.

The pre-processing section 112 performs, by using a notch filter or a band-pass filter, filtering processing on each positive-example waveform data and each negative-example waveform data acquired by the myoelectric signal acquisition section 111, thereby removing body motion noise and alternating-current noise components from each waveform data. Then, the pre-processing section 112 stores, in the myoelectric signal storage section 121, each positive-example waveform data and each negative-example waveform data after the filtering processing.

The characteristic amount calculation section 113 reads each positive-example waveform data and each negative-example waveform data from the myoelectric signal storage section 121 at predetermined sampling intervals and calculates a waveform characteristic amount from each waveform data for each read sample. For example, the characteristic amount is an amplitude characteristic amount or a frequency characteristic amount. Then, the characteristic amount calculation section 113 stores, for each of the positive and negative examples, data indicating the waveform characteristic amount calculated for each sample, in the characteristic amount storage section 122 in a temporally sequential manner.

In a projective transform model establishment phase, the node information update section 114 establishes a projective transform model based on the characteristic amount of each of the positive-example and negative-example waveform data stored in the characteristic amount storage section 122. The projective transform model projects a multi-dimensional vector expressed by a set of the characteristic amounts of the waveform data of each sample into a space (for example, a two-dimensional space) having a dimension lower than that of the multi-dimensional vector in accordance with, for example, self-organizing map approach. In a self-organizing map, a plurality of nodes each having a reference vector, and a projection table for projecting information of the nodes into a two-dimensional space are defined. Thus, the projective transform model is expressed by the node information and the projection table. Exemplary update processing of the node information will be described later in detail.

The projection table update section 115 transforms, by projecting, the characteristic amount of each of the positive-example and negative-example waveform data into a two-dimensional space for each sample based on the projective transform model learned by the node information update section 114 and calculates, from a result of the transform, the Euclidean distance between the positive-example data and the negative-example data for each sample in the two-dimensional space. Then, when the Euclidean distance is smaller than a threshold value, the projection table update section 115 performs update processing of the projection table. The update processing of the projection table is processing of moving the plot position of the negative-example data in the two-dimensional space so that the Euclidean distance is equal to or larger than the threshold value. Exemplary update processing of the projection table will be described later in detail.

When the Euclidean distance between the positive-example data and negative-example data becomes equal to or larger than the threshold value for all samples, the projection table update section 115 stores the node information and the projection table in this state in the projective transform model storage section 123 as information indicating the projective transform model.

In a state in which a motion state visualization phase is set after the projective transform model establishment phase ends, the motion state visualization section 116 reads, from the calculation section 113, the characteristic amount of the myoelectric signal waveform of the subject as a visualization target and the characteristic amount of a target myoelectric signal waveform corresponding to a target motion state. Then, the motion state visualization section 116 performs processing of transforming, by projecting, each read characteristic amount into the two-dimensional space in accordance with the projective transform model stored in the projective transform model storage section 123 and of outputting display data indicating a result of the transform from the interface unit 13 to the display device 3.

(Exemplary Operation)

The following describes exemplary operation of the motion state visualization device 1 configured as described above.

(1) Projective Transform Model Establishment Phase

When the projective transform model establishment phase is set, the motion state visualization device 1 executes learning processing for establishing the projective transform model as described below.

Figure 2:
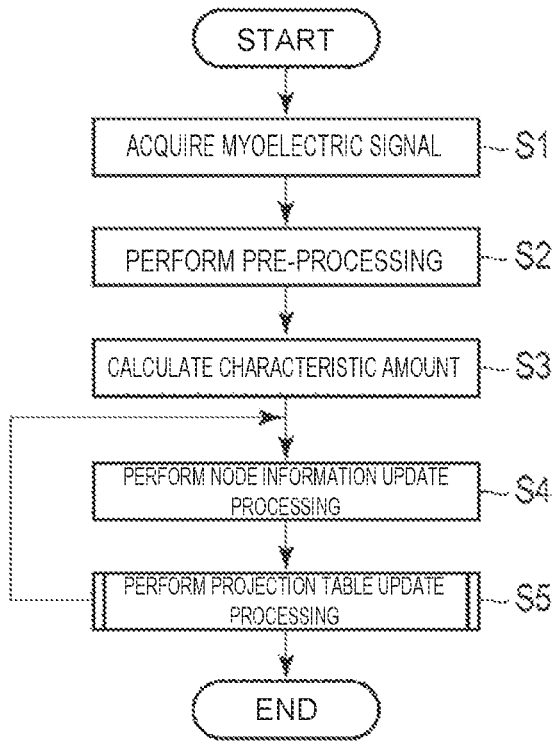
FIG. 2 is a flowchart illustrating an exemplary procedure and processing contents of processing of the motion state visualization device illustrated in FIG. 1 in a projective transform model learning phase.

FIG. 2 is a flowchart illustrating an exemplary processing procedure and processing contents of the projective transform model establishment phase by the control unit 11 of the motion state visualization device 1.

(1-1) Myoelectric Signal Acquisition and Pre-Processing

In the myoelectric signal measurement device 2, electrodes are mounted on a plurality of muscle sites corresponding to a monitoring-target muscle activity system of the subject, and continuous myoelectric signals are detected by the electrodes. In this case, each myoelectric signal detected in an ideal motion state of the subject is labeled as "positive example". Each myoelectric signal detected in a motion state detached from the ideal motion state of the subject is labeled as "negative example". In this example, the myoelectric signal measurement device 2 uses three electrodes, and accordingly, three sequential myoelectric signals EMG1, EMG2, EMG3 are output for each of the positive and negative examples.

At step S1, under control of the myoelectric signal acquisition section 111, the motion state visualization device 1 causes the interface unit 13 to receive three sequential myoelectric signals of the positive example and three sequential myoelectric signals of the negative example, which are output from the myoelectric signal measurement device 2 and transform the received signals into waveform data made of digital signals. The above-described transform processing into digital signals by the interface unit 13 is unnecessary when the myoelectric signal measurement device 2 has a function to transform a myoelectric signal from an analog signal to a digital signal.

Figure 5:
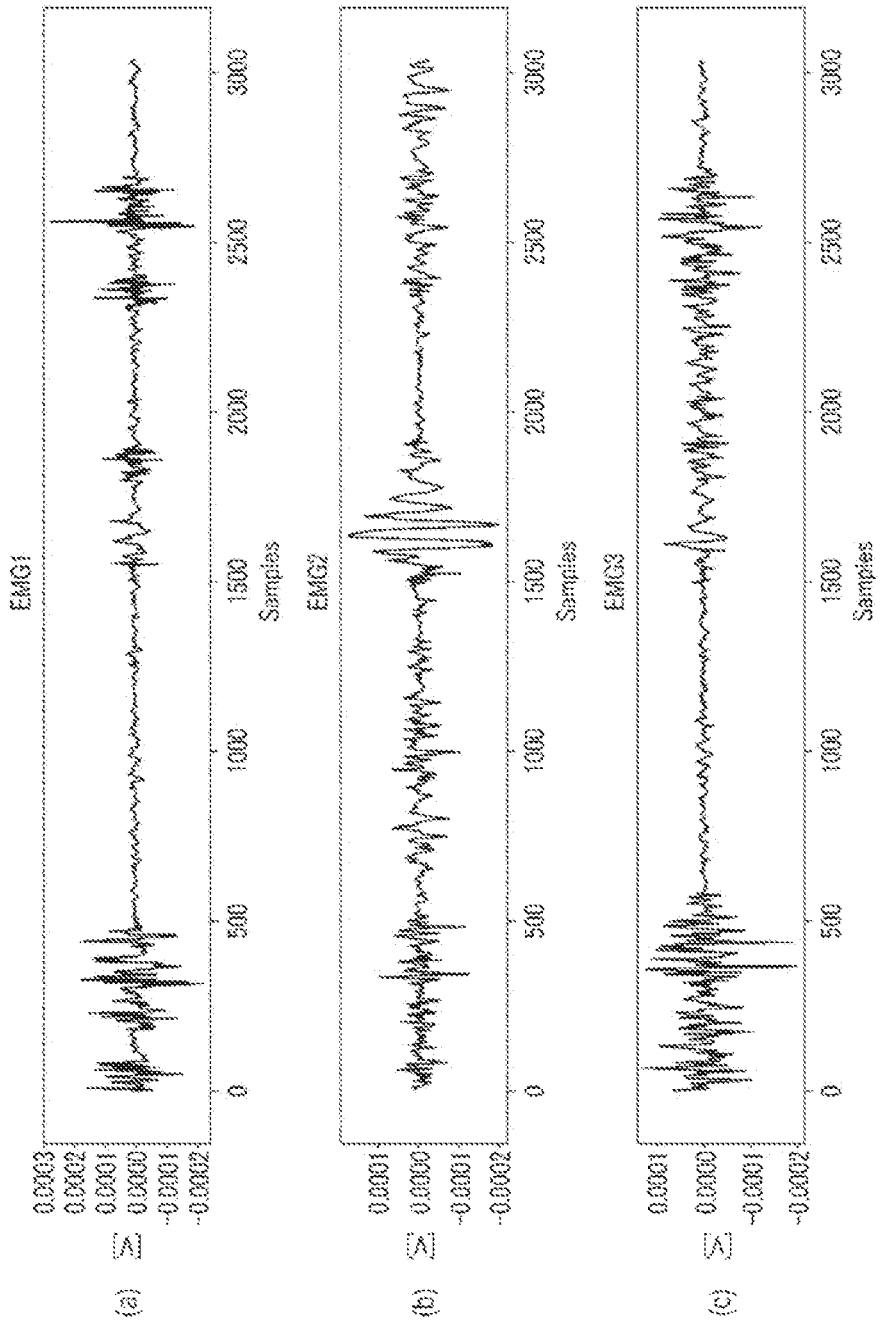
FIG. 5 is a diagram illustrating exemplary myoelectric signals (positive examples).
Figure 6:
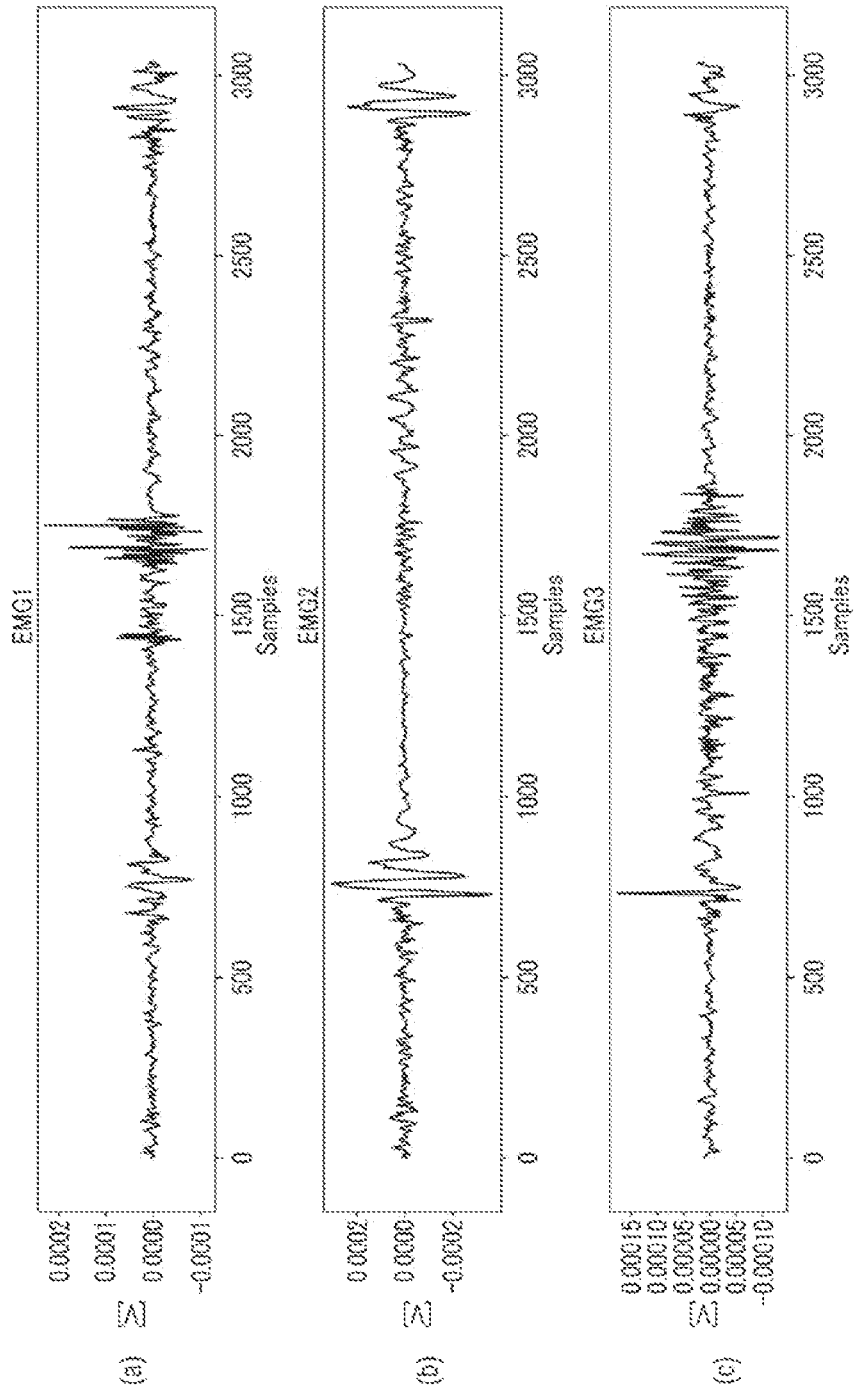
FIG. 6 is a diagram illustrating exemplary myoelectric signals (negative examples).

Subsequently at step S2, under control of the pre-processing section 112, the motion state visualization device 1 performs, by using a notch filter or a band-pass filter, filtering processing on the acquired three sequential waveform data of the positive example and three sequential waveform data of the negative example. As a result, body motion noise and alternating-current noise components included in each positive-example waveform data and each negative-example waveform data are removed. Then, the motion state visualization device 1 stores each positive-example waveform data and each negative-example waveform data after the filtering processing in the myoelectric signal storage section 121 in a temporally sequential manner. FIGS. 5(*a*), (*b*), and (*c*) illustrate exemplary positive-example waveform data after the filtering processing, and FIGS. 6(*a*), (*b*), and (*c*) illustrate exemplary negative-example waveform data after the filtering processing.

(1-2) Characteristic Amount Calculation

Subsequently at step S3, under control of the characteristic amount calculation section 113, the motion state visualization device 1 executes processing for extracting an amplitude characteristic amount from each of the positive-example waveform data and the negative-example waveform data as described below.

Specifically, the characteristic amount calculation section 113 reads each positive-example waveform data and each negative-example waveform data from the myoelectric signal storage section 121 at predetermined sampling intervals and calculates the amplitude characteristic amount from each waveform data for each read sample.

The amplitude characteristic amount may be calculated as, for example, a root mean square (RMS). When $d_1(i)$, $d_2(i)$, and $d_3(i)$ represent signals of a sample i among myoelectric signals (myoelectric waveform data) provided with the noise component removal processing and stored in the myoelectric signal storage section 121, RMS values $R_1(i)$, $R_2(i)$, $R_3(i)$ of the sample i are calculated by Formula below.

$$R_1(i) = \sqrt{\frac{1}{N}\sum_{j=0}^{N-1}[d_1(i+j)]^2}$$

$$R_2(i) = \sqrt{\frac{1}{N}\sum_{j=0}^{N-1}[d_2(i+j)]^2}$$

$$R_3(i) = \sqrt{\frac{1}{N}\sum_{j=0}^{N-1}[d_3(i+j)]^2}$$

[Formula 1]

In the formula, N represents the sample width of the RMS calculation and is set to be N=100 in this example.

Then, the characteristic amount calculation section 113 stores amplitude characteristic amount data $R_1$, $R_2$, and $R_3$ of all samples, which is calculated from each of the positive-example waveform data and the negative-example waveform data, in the characteristic amount storage section 122 in a temporally sequential manner. When n represents the sampling number, $R_1$, $R_2$, and $R_3$ are expressed as described below.

$$R_1=[R_1(1), R_1(2), \ldots, R_1(n)]$$

$$R_2=[R_2(1), R_2(2), \ldots, R_2(n)]$$

$$R_3=[R_3(1), R_3(2), \ldots, R_3(n)].$$

Figure 7:
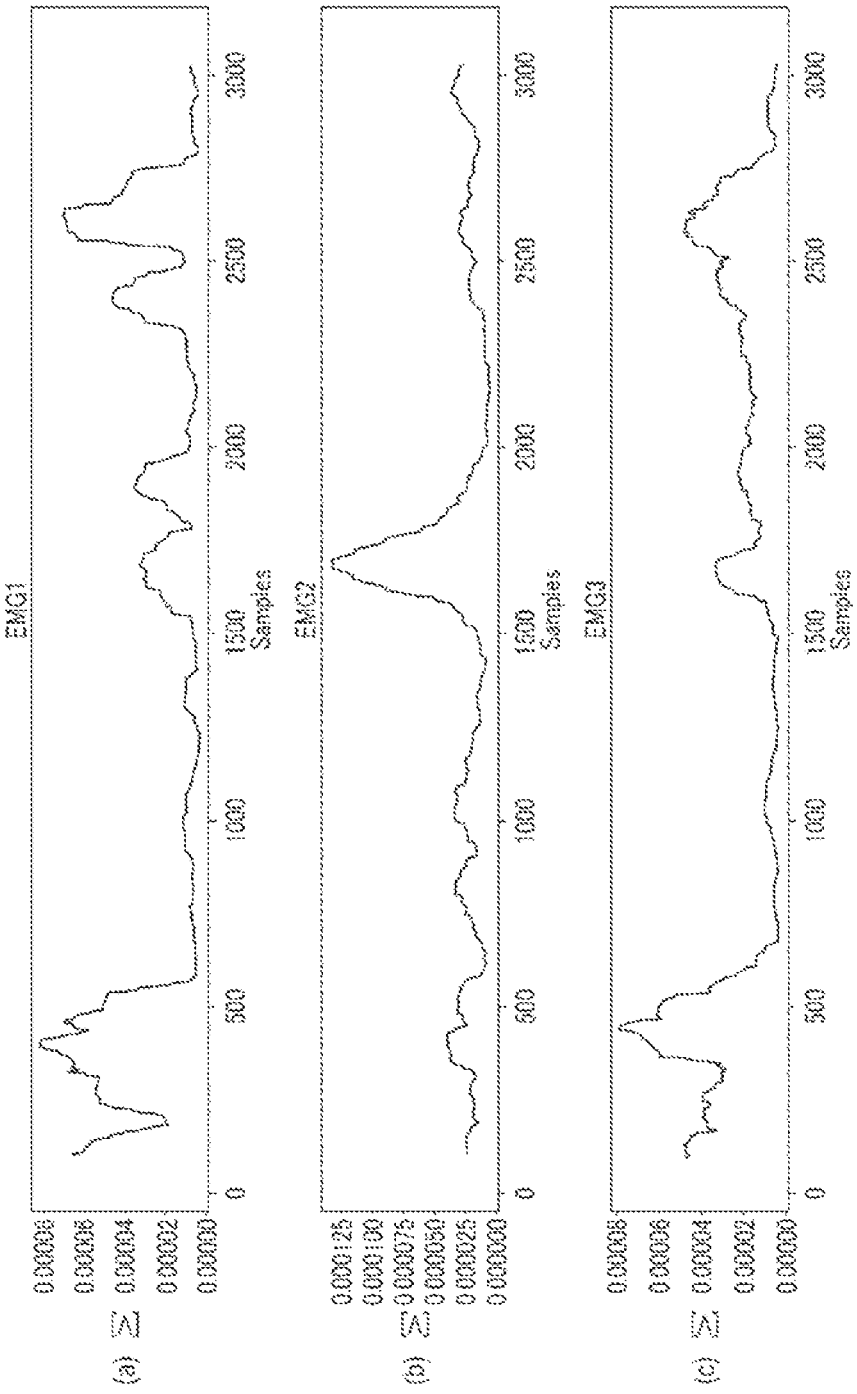
FIG. 7 is a diagram illustrating exemplary characteristic amounts (positive examples) calculated from the myoelectric signals illustrated in FIG. 5.
Figure 8:
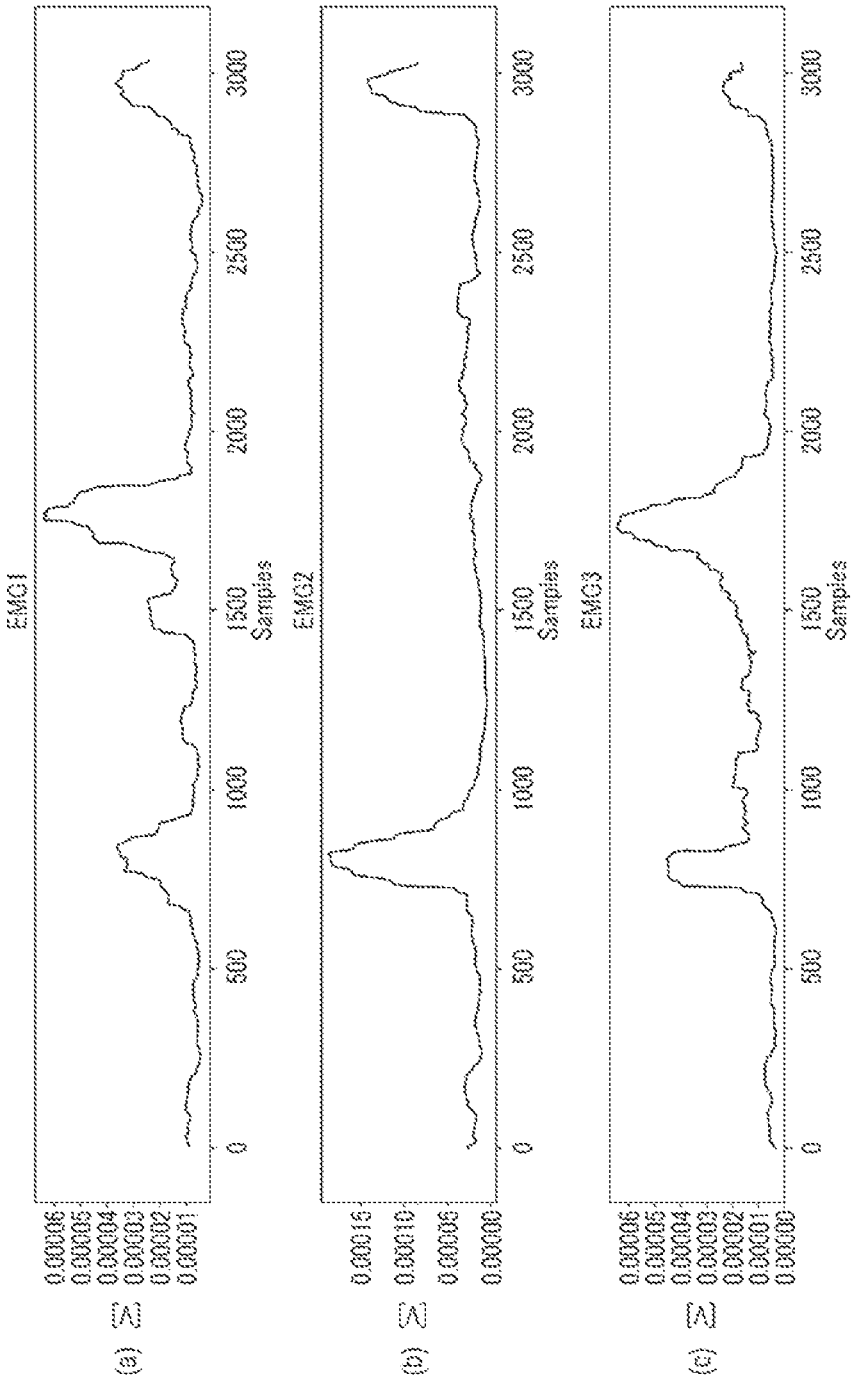
FIG. 8 is a diagram illustrating exemplary characteristic amounts (negative examples) calculated from the myoelectric signals illustrated in FIG. 6.

FIGS. 7(a), (b), and (c) illustrate exemplary temporally sequential data of RMS values calculated as the amplitude characteristic amount from each positive-example waveform data, and FIGS. 8(a), (b), and (c) illustrate exemplary temporally sequential data of RMS values calculated as the amplitude characteristic amount from each negative-example waveform data. The temporally sequential data of RMS values is also referred to as amplitude characteristic amount data. Instead of the amplitude characteristic amount, a frequency characteristic amount may be calculated as the characteristic amount of waveform data.

(1-3) Node Information Update

Subsequently, the motion state visualization device 1 performs learning processing for establishing the projective transform model based on the amplitude characteristic amount data $R_1$, $R_2$, and $R_3$ of each of the positive example and the negative example, which is stored in the characteristic amount storage section 122. In this example, self-organizing map approach is used to establish a model in which the three sequential amplitude characteristic amount data $R_1$, $R_2$, and $R_3$ of each of the positive example and the negative example is projected into the two-dimensional space for each sample.

A self-organizing map holds a plurality of nodes in a specified space, and each node has a reference vector having a dimension identical to that of input waveform data. In this example, the self-organizing map has 100 nodes. The nodes are referred to as $m_1$ to $m_{100}$.

When the k-th node is referred to as $m_k$, the node $m_k$ has a reference vector as follows.

$$m_k=[w_{k,1}, w_{k,2}, w_{k,3}]$$

In the vector, $w_{k,1}$, $w_{k,2}$, and $w_{k,3}$ represent reference vectors for the amplitude characteristic amount data $R_1$, $R_2$, and $R_3$, respectively, and are used to update the self-organizing map and project the input waveform data.

Figure 10:
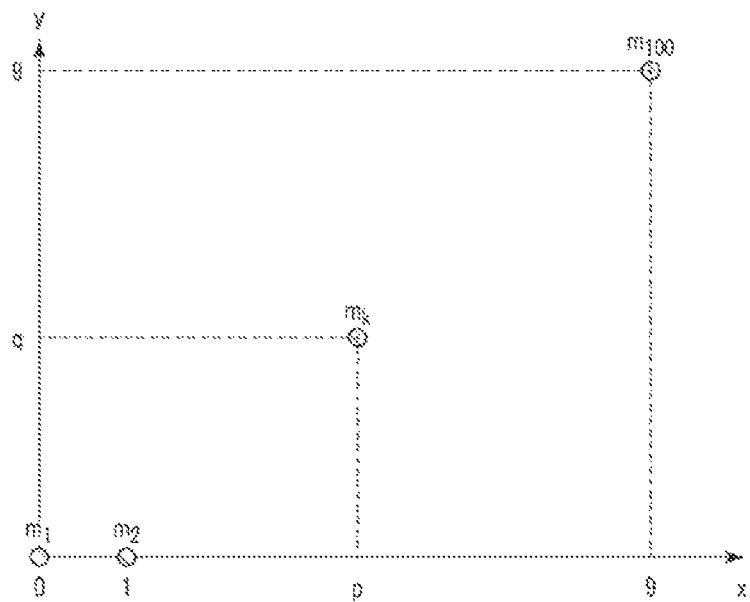
FIG. 10 is a diagram illustrating an exemplary two-dimensional space.

The self-organizing map has a projection table for projecting the nodes $m_1, \ldots, m_k, \ldots, m_{100}$ into the two-dimensional space. The projection table in the initial state has coordinate values set so that the nodes $m_1, \ldots, m_k, \ldots, m_{100}$ are equally dispersed in the two-dimensional space. FIG. 9 illustrates an exemplary projection table in this case. When this projection table is used, the k-th node $m_k$ is projected to a coordinate value (p, q) on a two-dimensional plane as illustrated in, for example, FIG. 10.

At step S4, under control of the node information update section 114, the motion state visualization device 1 reads, from the characteristic amount storage section 122, each of the three sequential amplitude characteristic amount data $R_1$, $R_2$, and $R_3$ of the positive example and the three sequential amplitude characteristic amount data $R_1$, $R_2$, and $R_3$ of the negative example for each sample, and updates the reference vectors of the nodes by using the amplitude characteristic amount data $R_1$, $R_2$, and $R_3$.

For example, when Sgood(i) represents data of the sample i in the amplitude characteristic amount data of the positive example and Sbad(i) represents data of the sample i in the amplitude characteristic amount data of the negative example, the data Sgood(i) and Sbad(i) of the sample i are expressed by Formulae below, respectively.

$$Sgood(i)=[R_1good(i), R_2good(i), R_3good(i)]$$

$$Sbad(i)=[R_1bad(i), R_2bad(i), R_3bad(i)]$$

The reading of the amplitude characteristic amount data $R_1good(i)$, $R_2good(i)$, $R_3good(i)$, $R_1bad(i)$ $R_2bad(i)$, and $R_3bad(i)$ is performed based on the labels of positive example and negative example provided to the amplitude characteristic amount data $R_1$, $R_2$, and $R_3$. The update processing of the reference vectors of the nodes based on the amplitude characteristic amount data Sgood(i) and Sbad(i) of the positive example and the negative example is disclosed in detail in Non-Patent Literature 1.

The motion state visualization device 1 outputs the node information holding the updated reference vectors and information indicating the projection table to the projection table update section 115 as the projective transform model.

(1-4) Projection Table Update

In the projection table in the initial state, the coordinate values of transform of the positive example and the negative example into the two-dimensional space are set to be values close to each other in some cases, and in such a case, the distance between plotted two-dimensional coordinates of the positive example and the negative example after the transform is short so that it is difficult to achieve differentiation therebetween.

Figure 3:
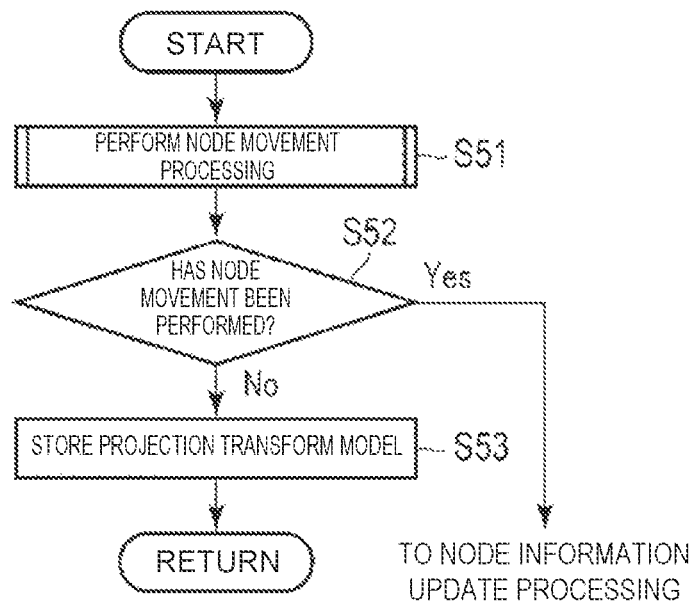
FIG. 3 is a flowchart illustrating an exemplary processing procedure and processing contents of projection table update processing in the projective transform model learning phase illustrated in FIG. 2.

Thus, at step S5, the projection table update section 115 executes update processing of the projection table as described below. FIG. 3 is a flowchart illustrating the procedure and processing contents of the processing.

Specifically, the projection table update section 115 reads the amplitude characteristic amount data $R_1$, $R_2$, and $R_3$ of the positive example and the amplitude characteristic amount data $R_1$, $R_2$, and $R_3$ of the negative example for each sample from the characteristic amount storage section 122. In addition, the projection table update section 115 receives the projective transform model including the node information and the projection table from the node information update section 114. Then, at step S51, the projection table update section 115 determines whether a coordinate value in the node information needs to be moved, and when it is determined that the coordinate value needs to be moved, the projection table update section 115 executes processing of moving the coordinate value of the node.

Figure 4:
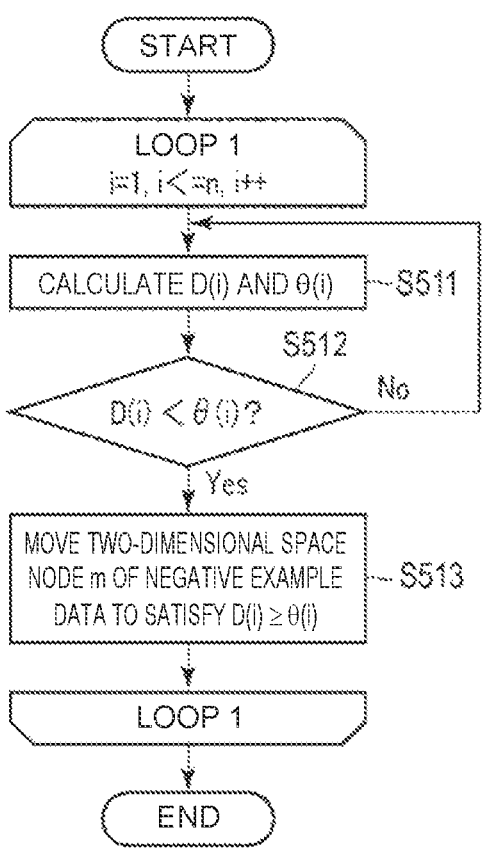
FIG. 4 is a flowchart illustrating an exemplary processing procedure and processing contents of node movement processing illustrated in FIG. 3.

FIG. 4 is a flowchart illustrating the procedure and processing contents of the node coordinate movement processing. The projection table update section 115 sequentially sets the sample i from 1 to n and performs, for each i, projective transform of the i-th sample in the amplitude characteristic amount data of each of the positive example and the negative example into the two-dimensional space based on the projection table. In the self-organizing map, nodes having reference vectors are dispersed, and the amplitude characteristic amount data is plotted to a node, the Euclidean distance of which is short.

For example, assume that the projection table is configured as illustrated in FIG. 9, and consider a case in which, under this condition, positive-example data Sgood(t) and Sgood(t') and negative-example data Sbad(t) and Sbad(t') in the (i=t)-th sample and the (i=t')-th sample, respectively, are as in Formulae below and the Euclidean distance is short.

$$Sgood(t) \rightarrow m_{33}$$

$$Sgood(t') \rightarrow m_{18}$$

$$Sbad(t) \rightarrow m_{75}$$

$$Sbad(t') \rightarrow m_{76}$$

Figure 11:
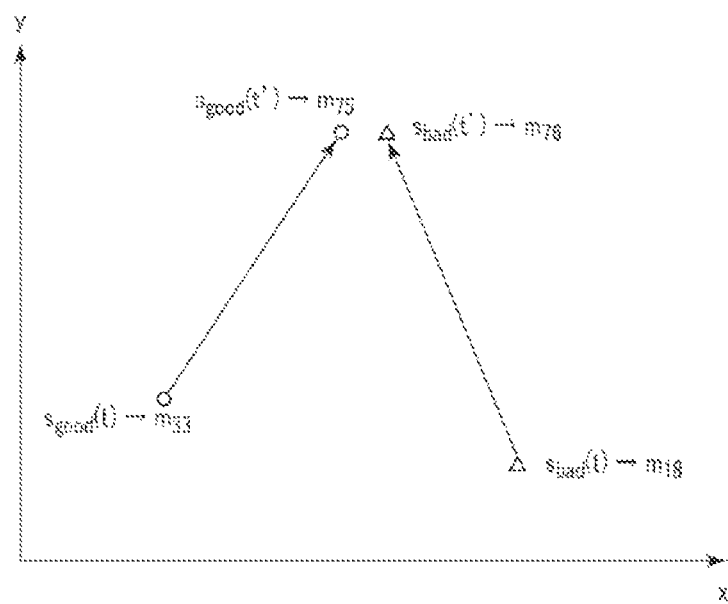
FIG. 11 is a diagram illustrating an example in which a coordinate value of each node expressed by the projection table illustrated in FIG. 9 is plotted in the two-dimensional space.

In this example, when transformed by projecting into the two-dimensional space, the positive-example data Sgood(t), Sgood(t') and the negative-example data Sbad(t), Sbad(t') are as illustrated in FIG. 11.

At step S511, the projection table update section 115 first calculates the Euclidean distance D for the positive-example data Sgood(t) and Sgood(t') and the negative-example data Sbad(t) and Sbad(t') in the two-dimensional space. In this case, the Euclidean distance D(t) between the positive-example data Sgood(t) and the negative-example data Sbad(t) of the t-th sample in the two-dimensional space is calculated by Formula below.

$$D(t) = \|m_{33} - m_{18}\| \quad \text{[Formula 2]}$$
$$= \sqrt{(2-7)^2 + (3-1)^2}$$
$$= \sqrt{29}$$

Similarly, the Euclidean distance D(t') between the positive-example data Sgood(t') and the negative-example data Sbad(t') of the t'-th sample in the two-dimensional space is calculated as follows.

$$D(t')=1$$

In addition, at step S511, the projection table update section 115 calculates a threshold value θ for determining the Euclidean distance D. In a case of the t-th sample, for example, the threshold value θ is calculated by using a correlation coefficient of the positive-example data and the Euclidean distance as follows.

$$\theta(t)=[1-\mathrm{corr}(s_{good(t)},s_{bad(t)})] \times \|(s_{good(t)},s_{bad(t)})\| \quad \text{[Formula 3]}$$

Subsequently at step S512, the projection table update section 115 compares the calculated Euclidean distance D(t) with the calculated threshold value θ(t). Then, when $$D(t)<\theta(t)$$

holds, the two-dimensional space coordinate of the node of the negative-example data is moved at step S513 so that the Euclidean distance D(t) between the node at which the negative-example data is plotted and the node at which the positive-example data is plotted is equal to or larger than the threshold value θ(t). When D(t) θ(t) holds, the two-dimensional space coordinate of the node of the negative-example data is not moved.

For example, in a case of $$\theta(t)=(\sqrt{15}) \text{ and}$$

$$\theta(t')=2,$$

D(t)≥θ(t) holds, and thus the two-dimensional space coordinate of the node $m_{18}$ is not moved. However, the Euclidean distance D(t') in the t'-th sample is D(t')=1, and it is determined that $$D(t')<\theta(t')$$

holds. Thus, the projection table update section 115 moves the coordinate value of the node $m_{76}$ to another coordinate value.

A node to be moved may be selected by any method, but, for example, the coordinate value of the node $m_{76}$ is moved in the X-axis direction until the condition of D(t')<θ(t') is satisfied. For example, the coordinate value of the node $m_{76}$ is moved to $m_{76}$=(6, 7).

When having ended the node movement processing at step S51, the projection table update section 115 determines whether any node is moved at step S52. As a result of the determination, when no node is moved, it is regarded that the update of the projection table is ended, the projection table is stored in the projective transform model storage section 123 at step S53.

When a node is moved, the projection table update section 115 updates the coordinate value of a projective transform destination corresponding to the node in the projection table to the coordinate value of the node after the movement. FIG. 12 illustrates the configuration of the projection table after the coordinate value of the node $m_{76}$ is moved.

When the projection table is updated, the projection table update section 115 feeds back the node information and the projection table after the update to the node information update section 114. The node information update section 114 updates the reference vector of the updated node based on the fed-back node information and projection table after the update.

The motion state visualization device 1 repeatedly executes the above-described series of processing (1-1) to (1-3) based on myoelectric signals provided by different subjects in predetermined motion, thereby learning the projective transform model. In this manner, the projective transform model is established.

(2) Motion State Visualization Phase

After the establishment of the projective transform model ends, the motion state visualization phase is set to the motion state visualization device 1. Thereafter, it is possible to perform processing of visualizing the motion state of a user by using the established projective transform model.

When the motion state of the user is to be visualized, the waveform data of a myoelectric signal corresponding to a target motion state for the user may be input to the motion state visualization device 1 in advance and stored in the myoelectric signal storage section 121.

(2-1) Myoelectric Signal Acquisition and Pre-Processing

In this state, the motion state visualization device 1 acquires three sequential myoelectric signals output from the myoelectric signal measurement device 2 mounted on the user through the interface unit 13 under control of the myoelectric signal acquisition section 111. In this case, the myoelectric signal is transformed into waveform data made of a digital signal by the interface unit 13.

Subsequently, under control of the pre-processing section 112, the motion state visualization device 1 performs filtering processing on the acquired three sequential waveform data by using a notch filter or a band-pass filter. As a result, body motion noise and alternating-current noise components included in each positive-example waveform data and each negative-example waveform data are removed. Then, the motion state visualization device 1 stores each waveform data after the filtering processing in the myoelectric signal storage section 121.

(2-2) Characteristic Amount Extraction

Subsequently, under control of the characteristic amount calculation section 113, the motion state visualization device 1 extracts the amplitude characteristic amount from the waveform data (measurement waveform data) of the measured myoelectric signal of the user, which is stored in the myoelectric signal storage section 121. In addition, the motion state visualization device 1 extracts the amplitude characteristic amount from the waveform data (target waveform data) of the myoelectric signal corresponding to the target motion state, which is stored in the myoelectric signal storage section 121. The amplitude characteristic amount of each waveform data is calculated as, for example, a root mean square (RMS) for each sample. The amplitude characteristic amount data calculated from the measurement waveform data and the amplitude characteristic amount data calculated from the target waveform data are temporarily stored in the characteristic amount storage section 122.

(2-3) Motion State Visualization Processing

Subsequently, under control of the motion state visualization section 116, the motion state visualization device 1 first reads the projective transform model from the projective transform model storage section 123. Then, the amplitude characteristic amount data calculated from the measurement waveform data and the amplitude characteristic amount data calculated from the target waveform data are read from the characteristic amount storage section 122, and each amplitude characteristic amount data is transformed, by projecting, into a coordinate in the two-dimensional space by using the projective transform model. Then, the motion state visualization section 116 generates display data for simultaneously displaying a two-dimensional space coordinate value corresponding to each amplitude characteristic amount data transformed by projecting, outputs the display data to the display device 3 through the interface unit 13, and causes the display device 3 to display the display data.

In this case, in the projection table of the projective transform model, the coordinate value of each node after the transform is updated and set so that the Euclidean distance D(i) between the positive-example data and the negative-example data in the two-dimensional space becomes equal to or larger than a threshold value θ(i). Accordingly, the distance between the two-dimensional coordinate value transformed by projecting based on the projection table of the projective transform model and indicating the measured motion state of the user and the two-dimensional coordinate value indicating the target motion state are displayed at positions sufficiently separated from each other in the two-dimensional space when the measured motion state is detached from the target motion state. Thus, when viewing the display data, the user can clearly understand the difference of the actual motion state of the user from the target motion state.

(Effects)

As described above in detail, a motion state visualization device according to the embodiment is provided with the projective transform model to which the self-organizing map is applied. The projective transform model includes a plurality of nodes holding a reference vector corresponding to multi-dimensional input data made of myoelectric signals, and a projection table indicating the correspondence relation between each node and the coordinate of the reference vector held by the node in a two-dimensional space into which the node is projected. Then, the motion state visualization device performs processing described below. Specifically, first in the learning phase of the projective transform model, the motion state visualization device acquires the multi-dimensional input data of each of a positive example and a negative example and calculates an amplitude characteristic amount from each multi-dimensional input data. Then, the motion state visualization device learns, as the reference vector of the nodes, the calculated amplitude characteristic amount data of each of the positive example and the negative example for each sample. Subsequently, the motion state visualization device calculates the Euclidean distance between coordinates when the nodes learned based on the amplitude characteristic amount data of the positive example and the nodes learned based on the amplitude characteristic amount data of the negative example are projected into the two-dimensional space in accordance with the projection table. Then, motion state visualization device updates coordinates in the projection table so that the calculated Euclidean distance becomes equal to or larger than a threshold value.

Thus, in the motion state visualization phase, when the characteristic amount corresponding to the actual motion state of a user and the characteristic amount corresponding to a target motion state are projected into the two-dimensional space by using the learned projective transform model, the projection coordinates of the actual motion state and the target motion state in the two-dimensional space can be displayed in a state in which the projection coordinates are separated from each other by an appropriate distance. Thus, by viewing the display, the user can clearly determine the difference between the actual motion state of the user and the target motion state.

[Modifications]

(1) The embodiment describes that the projective transform model transforms, by projecting into a two-dimensional space, characteristic amounts extracted from three sequential myoelectric signals. However, input signals are not limited to three sequential signals but may be two sequential signals or four or more sequential signals, and the projective transform destination may be another dimensional space such as a one-dimensional space or a three-dimensional space other than the two-dimensional space. Instead of using the self-organizing map, another method such as principal component analysis or multi-dimensional scaling may be applied as the method of transforming, by projecting, multi-dimensional information into a space having a dimension lower than that of the multi-dimensional information in the projective transform model.

(2) The embodiment describes the example in which characteristic amounts are extracted from a plurality of sequential myoelectric signals, respectively, and this multi-dimensional characteristic amount is transformed, by projecting, into visualization information indicating a body motion and having a dimension lower than that of the multi-dimensional characteristic amount. However, the present invention is not limited thereto but is also applicable to a case in which multi-dimensional information indicating various kinds of body motions, such as information indicating a cardiorespiratory motion, such as a heart rate signal or an electrocardiogram signal, information indicating a breathing state, and image information obtained by capturing motion of another body site such as head, eye, or mouth is acquired, and a characteristic amount extracted from the multi-dimensional information is transformed, by projecting, into visualization information having a dimension lower than that of the characteristic amount and visualized. In addition, the present invention is also applicable to a case in which multi-dimensional data indicating the operation state of a machine such as a manufacturing facility or a robot is transformed, by projecting, into data having a dimension lower than that of the multi-dimensional data and visualized.

(3) The embodiment describes the example in which the projective transform model learning phase and the motion state visualization phase are executed by one motion state visualization device 1. However, the present invention is not limited thereto, but the motion state visualization device may execute only the projective transform model learning phase, and the projective transform model learned by the motion state visualization device may be provided to, for example, the terminal device of the user by downloading so that the user can check the motion state of the user on the own terminal device. In this manner, a load on the terminal device can be reduced.

(4) The embodiment describes the example in which the display device 3 is a device different from the motion state visualization device 1, but a display device included in the motion state visualization device may be used when the motion state visualization device is configured by a terminal device having a display function, such as a personal computer, a smartphone, or a wearable terminal.

In addition, the kind and configuration of the motion state visualization device, the processing, procedure, and processing contents of the projective transform model learning phase, for example, may be modified in various manners without departing from the scope of the present invention.

In other words, the present invention is not limited to the above-described embodiments, but components thereof may be modified without departing from the scope thereof when executed for materialization. Moreover, various kinds of inventions may be achieved by appropriate combinations of a plurality of components disclosed in the above-described embodiments. For example, some components may be deleted from all components indicated in the embodiments. In addition, components in different embodiments may be combined as appropriate.

REFERENCE SIGNS LIST 1 motion state visualization device
2 myoelectric signal measurement device
3 display device
11 control unit
12 storage unit
13 interface unit
111 myoelectric signal acquisition section
112 pre-processing section
113 characteristic amount calculation section
114 node information update section
115 projection table update section
116 motion state visualization section
121 myoelectric signal storage section
122 characteristic amount storage section
123 projective transform model storage section

The invention claimed is:

1. A multi-dimensional data visualization device provided with a projective transform model including a plurality of nodes and a table, the plurality of nodes each holding a reference vector having a dimension identical to a dimension of input multi-dimensional data, the table storing information indicating a correspondence relation between each node and a coordinate in a projection target space, the multi-dimensional data visualization device comprising:
   a processor; and
   a storage medium having computer program instructions stored thereon, when executed by the processor, perform functions including:
   acquiring, by the processor, first and second multi-dimensional data for learning and extract characteristic amounts from the acquired first and second multi-dimensional data, respectively, the first and second multi-dimensional data including myoelectric signals passed through muscle fibers,
   the myoelectric signals detected by electrodes mounted on muscle sites, respectively,
   the acquired first and second multi-dimensional data including positive examples detected in an ideal motion state of the subject and negative examples detected in a motion state detached from the ideal motion state of the subject, and
   the characteristic amounts being one of amplitude characteristic amounts and frequency characteristic amounts extracted for each positive example and each negative example;
   updating, by the processor, the reference vector of each node based on the extracted characteristic amounts of the first and second multi-dimensional data;
   calculating, by the processor, based on the characteristic amounts of the first and second multi-dimensional data, a distance between each pair of coordinates when the updated nodes are projected into the projection target space in accordance with the table and update the table so that the distance is equal to or larger than a threshold value; and
   displaying, by the processor, motion of a subject on a display based on a result of the projection.

2. The multi-dimensional data visualization device according to claim 1, wherein the projective transform model includes, as the table, a table storing information indicating a correspondence relation between each node and a coordinate in a space having a dimension lower than the dimension of the multi-dimensional data.

3. The multi-dimensional data visualization device according to claim 1, wherein the projective transform model is established by applying a self-organizing map.

4. The multi-dimensional data visualization device according to claim 1 wherein the computer program instructions further perform to:
   acquire third and fourth multi-dimensional data as visualization targets and extract characteristic amounts from the acquired third and fourth multi-dimensional data, respectively; and
   input the extracted characteristic amounts of the third and fourth multi-dimensional data to the projective transform model after the nodes and the table are updated and generate and output display data for displaying a list of coordinates in the projection target space based on coordinates output from the projective transform model and corresponding to the third and fourth multi-dimensional data in the projection target space.

5. A multi-dimensional data visualization method executed by a device provided with a projective transform model including a plurality of nodes and a table, the plurality of nodes each holding a reference vector having a dimension identical to a dimension of input multi-dimensional data, the table storing information indicating a correspondence relation between each node and a coordinate in a projection target space, the multi-dimensional data visualization method comprising:
   acquiring, by one or more processors, first and second multi-dimensional data for learning and extracting characteristic amounts from the acquired first and second multi-dimensional data, respectively, the first and second multi-dimensional data including myoelectric signals passed through muscle fibers,
   the myoelectric signals detected by electrodes mounted on muscle sites, respectively, the acquired first and second multi-dimensional data including positive examples detected in an ideal motion state of the subject and negative examples detected in a motion state detached from the ideal motion state of the subject, and the characteristic amounts being one of amplitude characteristic amounts and frequency characteristic amounts extracted for each positive example and each negative example;

updating, the one or more processors, the reference vector of each node based on the extracted characteristic amounts of the first and second multi-dimensional data;

calculating, by the one or more processors, based on the characteristic amounts of the first and second multi-dimensional data, a distance between each pair of coordinates when the updated nodes are projected into the projection target space in accordance with the table and updating the table so that the distance is equal to or larger than a threshold value; and displaying, by the one or more processors, motion of a subject on a display based on a result of the projection.

6. The multi-dimensional data visualization method according to claim 5, further comprising:

acquiring third and fourth multi-dimensional data as visualization targets and extracting characteristic amounts from the acquired third and fourth multi-dimensional data, respectively; and inputting the extracted characteristic amounts of the third and fourth multi-dimensional data to the projective transform model after the nodes and the table are updated, and generating and outputting display data for displaying a list of coordinates in the projection target space based on coordinates output from the projective transform model and corresponding to the third and fourth multi-dimensional data in the projection target space.

7. The multi-dimensional data visualization method according to claim 5, wherein the projective transform model includes, as the table, a table storing information indicating a correspondence relation between each node and a coordinate in a space having a dimension lower than the dimension of the multi-dimensional data.

8. The multi-dimensional data visualization method according to claim 5 further comprising establishing the projective transform model by applying a self-organizing map.

9. A non-transitory computer-readable medium having computer-executable instructions that, upon execution of the instructions by a processor of a computer, cause the computer to function as the multi-dimensional data visualization device according to claim 1.

* * * * *